United States Patent [19]

Blount

[11] 4,011,253

[45] Mar. 8, 1977

[54] PROCESS FOR THE PRODUCTION OF SILICIC ACRYLATE COMPOUNDS AND RESINOUS PRODUCTS

[76] Inventor: David H. Blount, 5450 Lea St., San Diego, Calif. 92105

[22] Filed: July 9, 1976

[21] Appl. No.: 703,925

Related U.S. Application Data

[63] Continuation-in-part of Ser. Nos. 589,626, June 23, 1975, abandoned, and Ser. No. 551,534, Feb. 21, 1975, Pat. No. 3,956,466.

[52] U.S. Cl. .................... 260/448.2 E; 260/46.5 R; 260/448.2 Q; 260/448.8 R; 106/287 SB
[51] Int. Cl.² ...................... C07F 7/08; C07F 7/18
[58] Field of Search ............... 260/448.2 E, 46.5 R, 260/448.8 R, 448.2 Q

[56] References Cited

UNITED STATES PATENTS

| 3,674,430 | 7/1972 | Illigen et al. | 260/448.2 E UX |
| 3,826,814 | 7/1974 | Illigen et al. | 260/448.2 E UX |

*Primary Examiner*—Paul F. Shaver

[57] ABSTRACT

A dry granular alkali metal silicate is chemically reacted with a concentrated mineral acid or an acid hydrogen containing salt to produce a white granular silicic acid compound which will react chemically with an acrylic compound by using an alkaline compound as a catalyst, and by heating the mixture. The silicic acrylate compound is then polymerized with a catalyst such as a peroxide initiator.

9 Claims, No Drawings

PROCESS FOR THE PRODUCTION OF SILICIC ACRYLATE COMPOUNDS AND RESINOUS PRODUCTS

CROSS-REFERENCE TO RELATED CO-PENDING APPLICATION

This Application is a continuation-in-part of U.S. Pat. application Ser. No. 589,626, filed June 23, 1975, now abandoned and U.S. Pat. application Ser. No. 551,534, filed Feb. 21, 1975, now U.S. Pat. No. 3,956,466, dated May 11, 1976.

BACKGROUND OF THE INVENTION

This invention relates to a process for the production of silicic acrylate compounds and their resinous products by chemically reacting a silicic acid compound with an acrylic compound to produce a silicic acrylate compound. The silicic acrylate compound may then be polymerized with a catalyst such as a peroxide initiator.

The silicic acid compound used in this process may be produced by the chemical reaction of a dry alkali metal metasilicate with a mineral acid or an acid hydrogen containing salt. The silicic compound produced by this method was analyzed and contained hydrogen, oxygen and silicon in the ratio of about 2 mols of hydrogen to about 2 mols of oxygen to 1 mol silicon. The silicic acid used on the following examples was produced by reacting dry granular alkali metal metasilicate with an hydrogen containing acid salt or a concentrated mineral acid. The white granular silicic acid is washed with water, filtered and then air dried at 25° to 75° C. The white granular silicic acid was analyzed by infrared analysis, using the 1R KBr disc method. The infrared analysis was very similar to that obtained with Mallinckrodt's hydrated silica except for the area which shows the presence of Si—H bonds. The Mallinckrodt's hydrated silica ($SiO_2 \cdot _xH_2O$) has a molecular weight of $60.09 \cdot _xH_2O$. The said silicic acid contains an active hydrogen which will reduce silver nitrate in an aqueous solution which is evident that Si—H bonds are present.

When the said silicic acid is heated to much above 105° C, silicon dioxide with a molecular weight of about 60 is produced. On further heating, it has a melting point of 1650° C. In cryoscopic and ebullioscopic determination, the silicic acid produced was not soluble in any common organic solvent but was readily soluble in dilute alkali metal hydroxide aqueous solutions.

The molecular weight was determined from the boiling point elevation of said silicic acid in a 6N sodium hydroxide solution and indicated a molecular weight of 78 ± 25gm/mol. This type of reactive solution normally changes the molecular species. However, this would seem to indicate the absence of a polymeric form of silicate. This analysis may indicate a possible formula of $H Si(OH)_3$ (orthosilicoformic acid) and the presence of some metasilicic acid ($H_2SiO_3$) while in solution. The orthosilicoformic acid when dried will lose water to form silicoformic acid (H.SiO.OH).

To produce the silicic acid compound used in this process, it is necessary to use a dry alkali metasilicate instead of using an aqueous solution of an alkali metasilicate to avoid producing silicic acid gel, silica and/or silicon dioxide. I have performed experiments reacting an aqueous solution of sodium metasilicate with an acid to produce silicic acid gel, silica and silicon dioxide, then by using the same procedure as used in my examples, I have been unable to react chemically dry granular silicic acid gel, silica or silicon dioxide with an acrylic compound. The silicic compound produced by my process reacts chemically with the acrylic compound, and when polymerized it produces a poly(silicic acrylate) polymer; the silicic acid compound produced in my process does not precipitate out and is soluble in many solvents.

The exact course of the reactions which take place during the process to produce poly(silicic acrylate) polymers cannot be determined with 100% certainty.

The silicic acrylate compounds may be co-polymerized with other polymerable compounds such as methyl methacrylte, styrene, allylchloride, acrylonitrile, vinyl chloride, butadiene and other polymerizable compounds.

The silicic acrylate resinous products produced in my process may be ground into a powder, softened with heat and then molded into useful products. The silicic acrylate resinous products are soluble in common solvents such as aqueous ammonium solution, acetic acid, alcohols, dilute sulfuric acid, alkali metal hydroxide solutions, acetone and other organic solvents. A solution of the silicic acrylate resinous products may be painted on wood and used as an adhesive or a tough protective coating. The silicic acrylate resinous products will form dispersions in aqueous solutions and may be painted on wood and forms a tough protective coating when dried.

SUMMARY OF THE INVENTION

I have discovered that a silicic acid compound produced by the chemical reaction of a dry alkali metal metasilicate with a concentrated mineral acid or an acid hydrogen containing salt will react chemically with an acrylic acid compound such as acrylic acid, methacrylic acid, ethyl acrylic acid, bromoacrylic acid, chloroacrylic acid, hydracrylic acid and benzyl acrylic acid. Best results occur when about equal weight of the reactants are used. In the polymerization process, the silicic compound apparently also acts as the cross-linking agent.

Various alkaline metal and alkali metal metasilicates may be used in the process but dry granular sodium metasilicate is preferred.

Various mineral acids and acid hydrogen containing salts may be used in this process, but concentrated sulfuric acid (60–98%) and sodium hydrogen sulfate are preferred.

Various alkali compounds such as alkali metal carbonates, hydroxides, oxides and alkali metal salts of weak acids may be used as the catalyst in the chemical reaction to produce silicic acrylate compounds. The most useful alkali metal carbonates is sodium carbonate, but other alkali metal carbonates such as potassium carbonate may be used. The most useful alkali metal hydroxide is sodium hydroxide, but potassium hydroxide and othr alkali metal hydroxides may be used as the catalyst. Sodium silicate may also be used as the catalyst. Best results are obtained when the alkali catalyst is added in the amount of 1% to 10% of the weight of the reactants, silicic acic compound and acrylic compound.

Various peroxide initiators may be used such as potassium persulfate, ammonium persulfate, hydrogen peroxide, cumene hydroperoxide, p-menthane hydroperoxide, potassium and ammonium persulfate with ferric sulfate or cupric sulfate, and others. A redox system of initiation may be used. Benzoyl peroxide with a tertiary amine activator, such as N,N-dimethyl aniline may be used. Anionic agents will polymerize silicic acrylate compounds. Organic peroxides and hydroperoxides such as ethyl ketone peroxide with cobalt naphthenate, benzoyl peroxide, acetyl benzoly peroxide, p-chlorobenzoyl peroxide, alkoxy benzol peroxide, lauroryl peroxide, dibutyryl peroxide, dicaproyl peroxide, crotonyl peroxide, di-tert-alkyl peroxides, methyl amyl ketone peroxide, di-tert butyl diphosphate peroxide, peracetic acid and cyclohexyl hypoperoxide may be used.

The silicic acrylate compounds produced by this process may be copolymerized with vinyl chloride, vinylidine chloride, vinyl acetate acrylonitril, methyl methacrylate, cyclohexyl-cyclohexyl methacrylate, allyl methacrylate, allyl chloride, maleic anhydride, polyester resins, polyether resins, polyurethane resins, acrylic acid, methacrylic acid, ethyl acrylic acid and others.

I have discovered that silicic acrylate compounds can also be produced from methyl methacrylate by alcoholysis. The silicic acid compound produced by this process may be reacted with methyl methacrylate by heating the reactants with an alkali catalyst; there is an exchange of silicic acid compound for the methyl group, thereby producing methyl silicic acrylate.

The primary object of the present invention is to produce silicic acrylate compounds and resinous products. Another object is to produce silicic acrylate compounds that can be copolymerized with unsaturated organic chemicals to form new resins. Still another object is to produce useful molding powders. A further object is to produce silicic acrylate compunds and resinous compounds that are readily soluble in aqueous or organic solvents and may be used as a protective coating on wood.

DESCRIPTION OF PREFERRED EMBODIMENTS

My invention will be illustrated in greater detail by the specific examples that follow, it being understood that these preferred embodiments are illustrative of, but not limited to, procedures which may be used in the production of silicic acrylate compounds and resinous products. Parts and percentages are by weight unless otherwise indicated.

EXAMPLE I

About 150 parts by weight of sodium metasilicate pentahydrate are slowly added to about 75 parts by weight of concentrated sulfuric acid while agitating and keeping the temperature below 100° C. The reaction takes place under ambient pressure; oxygen is evolved and the reaction is complete in 1 to 2 hours, thereby producing a white granular silicic acid compound and sodium sulfate. The mixture is washed with water, filtered to remove the salt and water, thereby recovering the silicic acid compound. The silicic acid compound is air dried at 25° to 75° C.

About 80 parts by weight of the said silicic acid compound and about 72 parts by weight of acrylic acid are mixed together, and a catalyst, sodium carbonate, is added in the amount of about 5 parts by weight. The mixture is then heated to about 90° C at ambient pressure while agitating for about 30 minutes until the chemical reaction is complete, thereby producing tan granules of silicic acrylate.

To polymerize the silicic acrylate, about 200 parts by weight of water, about 1 part by weight of potassium persulfate, and about 0.02 parts by weight of ferric sulfate are added to the tan granules of silicic acrylate. The mixture is then heated to about 80° C while agitating, and the reaction is completed in about 60 minutes, thereby producing a light tan poly(silicic acrylate) polymer.

The resulting poly(silicic acrylate)polymer is soluble in acetic acid, alcohol, dilute sulfuric acid, dilute alkali hydroxide solution and ammonium hydroxide solutions. It will form emulsions with water. It is precipitated from the emulsion by adding dilute hydrochloric acid until the pH is about 5 to 6.

EXAMPLE II

About 120 parts by weight of the silicic acid compound produced in Example I and about 72 parts by weight of acrylic acid are mixed together and about 6 parts by weight of a catalyst, sodium carbonate, is added The mixture is heated to 70° to 90° C while agitating for about 30 to 40 minutes, under ambient pressure, thereby producing light tan granules of silicic acrylate. About 20 to 30 parts by weight of the silicic acid compound has not reacted with the acrylic acid.

To polymerize the mixture of tan granules of silicic acrylate and the silicic acid compound, about 300 parts water, about 1.5 parts potassium persulfate, and about 0.02 parts cupric sulfate are added, all by weight, to the silicic acrylate. The mixture is heated to about 50° to 75° C while agitating for about 40 to 60 minutes until the reaction is complete, thereby producing poly(silicic acrylate) resin. The above unreacted silicic compound appears to chemically act as the cross linking agent.

The poly(silicic acrylate) resin will form an emulsion with water and when painted on wood, forms a hard tough protective coating. The poly(silicic acrylate) resin will precipitate from the aqueous emulsion by the addition of an acid or base to the emulsion. The said resin is not soluble in water, mineral acids, alkali metal hydroxides or acrylic acid. The resin will soften with heat but does not melt.

The aqueous emulsion of poly(silicic acrylate) resin which was obtained when the above silicic compound and acrylic acid was polymerized, was filtered and only 5 to 10 parts by weight of the 120 parts of silicic acid compound was filtered out unreacted.

EXAMPLE III

About 80 parts by weight of the silicic acid compound produced in Example I and about 86 parts by weight methacrylic acid are mixed with about 4 parts by weight of a catalyst, sodium carbonate. The mixture is heated to about 80° to 100° C while agitating at ambient pressure for about 20 minutes until the chemical reaction is complete, thereby producing light tan granules of silicic methacrylate.

To polymerize the tan granules of silicic methacrylate, about 300 parts water, about 2 parts potassium persulfate, and about 0.05 parts ferric sulfate are added by weight, to the silicic methacrylate granules, then heated to about 50° C while agitating for about 60 minutes until the reaction is complete, thereby producing poly(silicic methacrylate) polymer, in the form of an aqueous emulsion. The aqueous emulsion was filtered and about 5 to 10 parts of the silicic acid compound was filtered out unreacted.

The poly(silicic methacrylate)polymer is precipitated from the emulsion by the addition of dilute hydrochloric acid until the pH is about 6 to 7. The poly(silicic methacrylate) polymer is soluble in ammonium hydroxide aqueous solution and may be painted on wood and forms a tough protective coating when dry.

EXAMPLE IV

About equal parts by weight of a dry potassium metasilicate containing less than 6 mols of water per mol of potassium metasilicate and potassium hydrogen sulfate are mixed. The mixture is agitated at ambient pressure and the chemical reaction causes oxygen to evolve in 1 to 3 minutes; considerable heat is produced, and the chemical reaction is complete in 1 to 2 hours, thereby producing white granules of a silicic acid compound and potassium sulfate. The mixture is washed with water and filtered to remove the salt. The silicic acid compound is air dried at 25° to 75° C.

About 80 parts by weight of said silicic acid compound and about 100 parts of weight ethyl acrylic acid are mixed, and about 8 parts by weight of a catalyst, sodium hydroxide is added. The mixture is heated to just below the boiling point of ethyl acrylic acid while agitating for about 40 minutes until the chemical reaction is completed, thereby producing light tan granules, silicic ethyl acrylate.

To polymerize the silicic ethyl acrylate, about 400 parts water, about 1 to 3 parts ammonium persulfate, about 1 to 2 parts sodium thiosulfate and about 0.01 parts cupric sulfate are added, all by weight. The mixture is heated to about 60° C while agitating for about 60 minutes until the reaction is complete, thereby producing an emulsion of poly(silicic ethyl acrylate) polymer.

EXAMPLE V

About 120 parts by weight of the silicic acid compound produced in Example IV and about 85 parts methacrylic acid are mixed. A catalyst, potassium carbonate, is added in the amounts of about 7 parts by weight. The mixture is heated to just below the boiling point of methacrylic acid while agitating for about 40 minutes until the chemical reaction is complete, thereby producing a mixture of silicic methacrylate and silicic acid compound. About 0.5 parts by weight of cobalt naphthenate and about 0.3 parts by weight of methyl ethyl ketone peroxide are added to the mixture, mixed, and the temperature is maintained between 35° to 50° C for about 10 to 30 minutes, thereby producing poly(silicic methacrylate) polymer.

EXAMPLE VI

About 80 parts by weight of the silicic acid compound produced in Example I and about 100 parts by weight of chloroacrylic acid are mixed. About 6 parts by weight of a catalyst, sodium metasilicate is added. The mixture is heated to just below the boiling point of chloroacrylic acid for about 40 minutes until the chemical reaction is complete, thereby producing granules of silicic chloroacrylate.

To polymerize the silicic chloroacrylate granules, 0.5 parts by weight of benzoyl peroxide is mixed with the silicic chloroacrylate and then heated to 50° to 150° C for 10 to 40 minutes until the polymerization is complete, thereby producing poly(silicic chloroacrylate polymer.

EXAMPLE VII

About 80 parts by weight of the silicic acid compound produced in Example IV and about 150 parts by weight of benzyl acrylic acid are mixed together, and about 6 parts by weight of a catalyst, sodium benzyl acrylate is added. The mixture is heated to about 90° to 100° C wile agitating for about 45 minutes until the chemical reaction is complete, thereby producing granules of silicic benzyl acrylate.

To polymerize the granules of silicic benzyl acrylate, about 200 parts of water, 0.2 parts of tert-dodecyl mercaptan, 0.15 parts of ferrous sulfate heptahydrate, 5 parts of potassium salt of disproportionated rosin and 1 part of potassium pyrophosphate are added by weight to the above mixture; it is then heated to about 80° C while agitating, and the reaction is complete in about 90 minutes, thereby producing poly(silicic benzyl acrylate) polymer.

EXAMPLE VIII

About 80 parts by weight of the silicic acid compound produced in Example IV and 150 parts by weight of cyclohexyl acrylic acid are mixed; then about 5 parts by weight of a catalyst, potassium hydroxide is added. The mixture is then heated to about 80° to 90° C while agitating for 45 minutes until the chemical reaction is complete, thereby producing granules of silicic cyclohexyl acrylate.

To polymerize the granules of silicic cyclohexyl acrylate, about 200 parts of water, 4 parts of potassium fatty acid soap, 0.2 parts of O-methane hydroperoxide, 0.01 parts of ferrous sulfate heptahydrate, 0.2 parts of diethylenetriamine, 0.2 parts of tert-dodecyl mercaptan, and 1 part trisodium phosphate dodecahydrate are added by weight then mixed and heated to about 70° C while agitating, and the reaction is complete in about 80 minutes, thereby producing poly(silicic cyclohexyl acrylate) polymer.

EXAMPLE IX

About 100 parts by weight of granular sodium metasilicate containing less than 6 mols of water per mol of sodium metasilicate is slowly added to 100 parts by weight of concentrated sulfuric acid while agitating and keeping the temperature below 100° C. The chemical reaction is complete in 1 to 2 hours, thereby producing a white granular silicic acid compound and sodium hydrogen sulfate. The mixture is washed with water, filtered to remove the sodium hydrogen sulfate and recover the white granular silicic acid compound. The silicic acid compound is air dried at 25° to 75° C by blowing air thru the granules.

About 40 parts by weight of the said silicic acid compound are mixed with 80 parts by weight of acrylic acid and about 6 parts by weight of a catalyst, potassium carbonate, are added. The mixture is then heated to just below the boiling point of acrylic acid while agitating at ambient pressure for 30 to 45 minutes, thereby producing poly(silicic acrylate) polymer.

I claim:

1. The process for the production of silicic acrylate compounds and resinous products by the following steps:

(a) adding about 100 parts by weight of dry granular alkali metal metasilicate slowly to 50 parts by weight of concentrated sulfuric acid (60–98% acid)

(b) agitating said mixture to keep the temperature below 100° C and oxygen evolves from the mixture, thereby (c) producing a white granular mixture of a silicic acid compound and alkali metal sulfate;

(d) washing said mixture with water, then filtering the mixture to remove the alkali metal sulfate and then air drying at 25° to 75° C., leaving a fine white granular silicic acid compound;

(e) mixing about 50 parts by weight of said silicic acid compound with about 30 to 95 parts by weight of an acrylic acid compound;

(f) adding an alkali catalyst in the ratio of 1% to 10% by weight of the silicic acid compound and acrylic acid compound;

(g) heating the said mixture to just below the boiling point of the acrylic acid compound while agitating for about 20 to 60 minutes, thereby (h) producing a tan granular silicic acrylate compound.

2. The process according to claim 1, further including the steps of adding a catalytic amount of a peroxide initiator to said silicic acrylate compound; heating said mixture to a temperature of from about 30° to 120° C while agitating for at least about 10 minutes, whereby a poly(silicic acrylate) polymer is produced.

3. The process according to claim 1 wherein the dry alkali metasilicate is selected from the group consisting of sodium metasilicate and potassium metasilicate.

4. The process according to claim 1 wherein the acrylic acid compound is selected from the group consisting of acrylic acid, methacrylic acid, ethyl acrylic acid, benzyl acrylic acid, chloroacrylic acid and cyclohexyl acrylic acid.

5. The process according to claim 1 wherein the alkali catalyst is selected from the group consisting of sodium carbonate, potassium carbonate, sodium hydroxide, potassium hydroxide, sodium acrylate and sodium silicate.

6. The process according to claim 2 wherein the peroxide initiator is selected from the group consisting of hydrogen peroxide, potassium persulfate, ammonium persulfate, cumene hydroperoxide benzoyl peroxide, ethyl ketone peroxide with cobalt naphthenate and o-menthane hydroperoxide.

7. The process according to claim 2 wherein the peroxide initiator is potassium persulfate, 0.5 to 1.5 parts by weight, and ferric sulfate, 0.01 to 0.02 parts by weight carbonate 100 parts by weight of the silicic acrylate compound; the reaction takes place in an aqueous solution of 200 to 400 parts other weight of water and is agitated for 30 to 80 minutes, thereby producing an aqueous emulsion of the poly(silicic acrylate) polymer. acid 8. The process according to claim 2 wherein the peroxide initiator is utilized in a redox system, consisting of 200 to 400 parts water, 1 to 3 parts ammonium persulfate, about 0.01 parts cupric sulfate and about 1 to 2 parts sodium thiosulfate per 100 parts of the silicic acrylate compound; the mixture is agitated for about 60 minutes.

9. The process according to claim 6 wherein an additional step of adding dilute hydrochloric acid to the poly(silicic acrylate) polymer until the pH is about 6 to 7, thereby precipitating the poly(silicic acrylate) polymer.

* * * * *